(12) United States Patent
Nagai et al.

(10) Patent No.: US 9,795,967 B2
(45) Date of Patent: Oct. 24, 2017

(54) SAMPLE ANALYZER AND REAGENT CONTAINER

(71) Applicant: Sysmex Corporation, Kobe-shi, Hyogo (JP)

(72) Inventors: Takaaki Nagai, Kobe (JP); Noriyuki Nakanishi, Kobe (JP); Mitsuo Yamasaki, Kobe (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 168 days.

(21) Appl. No.: 14/664,182

(22) Filed: Mar. 20, 2015

(65) Prior Publication Data

US 2015/0273466 A1    Oct. 1, 2015

(30) Foreign Application Priority Data

Mar. 28, 2014  (JP) .................................. 2014-069375

(51) Int. Cl.
  *B01L 3/00*  (2006.01)
  *B01L 9/00*  (2006.01)
  (Continued)

(52) U.S. Cl.
  CPC ............. *B01L 3/508* (2013.01); *B01L 3/0293* (2013.01); *B01L 3/523* (2013.01); *B01L 9/00* (2013.01);
  (Continued)

(58) Field of Classification Search
  CPC ......... B01L 2200/025; B01L 2200/141; B01L 2200/16; B01L 2300/041;
  (Continued)

(56) References Cited

U.S. PATENT DOCUMENTS

2003/0129094 A1*  7/2003  Schubert ............... B01L 3/5085
                                                            422/501
2005/0074363 A1*  4/2005  Dunfee .............. G01N 35/1004
                                                             422/81

(Continued)

FOREIGN PATENT DOCUMENTS

DE         43 14 657 A1    11/1994
JP         2003-083998      3/2003
                (Continued)

*Primary Examiner* — Sean E Conley
*Assistant Examiner* — Benjamin R Whatley
(74) *Attorney, Agent, or Firm* — Brinks Gilson & Lione

(57) ABSTRACT

A sample analyzer comprises a reagent container setting part configured to install a reagent-container retainer for retaining a reagent container having an opening, an aspirating tube configured to aspirate a reagent in the reagent container, and an aspirating tube holder configured to hold the aspirating tube. The aspirating tube holder includes a cover, the cover having an open portion provided from a bottom face thereof to a side face thereof, the cover covering the aspirating tube with a region thereof other than the open portion. The aspirating tube holder includes a guide portion configured to guide the aspirating tube holder relative to the reagent-container retainer such that the aspirating tube holder is allowed to reach a state where the aspirating tube has entered the reagent container or a state where the aspirating tube has retreated from the reagent container.

19 Claims, 25 Drawing Sheets

(51) Int. Cl.
*B01L 3/02* (2006.01)
*G01N 35/10* (2006.01)
*G01N 35/00* (2006.01)

(52) U.S. Cl.
CPC ..... *G01N 35/1002* (2013.01); *G01N 35/1011* (2013.01); *B01L 2200/025* (2013.01); *B01L 2200/141* (2013.01); *B01L 2200/16* (2013.01); *B01L 2300/041* (2013.01); *B01L 2300/0809* (2013.01); *G01N 2035/00277* (2013.01); *G01N 2035/00306* (2013.01)

(58) Field of Classification Search
CPC .......... B01L 2300/0809; B01L 3/0293; B01L 3/508; B01L 3/523; B01L 9/00; G01N 2035/00277; G01N 2035/00306; G01N 35/1002; G01N 35/1011
See application file for complete search history.

(56) References Cited

U.S. PATENT DOCUMENTS

| | | | |
|---|---|---|---|
| 2005/0123445 A1* | 6/2005 | Blecka | G01N 35/0099 422/64 |
| 2010/0080732 A1 | 4/2010 | Mototsu et al. | |
| 2012/0321513 A1 | 12/2012 | Nagai et al. | |

FOREIGN PATENT DOCUMENTS

| | | |
|---|---|---|
| WO | WO 91/01007 A1 | 1/1991 |
| WO | WO 2011/105247 | 9/2011 |

* cited by examiner

SAMPLE ANALYZER AND REAGENT CONTAINER

CROSS REFERENCE TO RELATED APPLICATIONS

This application claims priority from prior Japanese Patent Application No. 2014-069375, filed on Mar. 28, 2014, entitled "SAMPLE ANALYZER AND REAGENT CONTAINER", the entire content of which is incorporated herein by reference.

FIELD OF THE INVENTION

The present invention relates to sample analyzers and reagent containers.

BACKGROUND

Conventionally, there have been known sample analyzers which analyze samples by use of reagents in reagent containers (see International Publication WO 2011/105247, for example).

International Publication WO 2011/105247 above discloses an analyzer that includes: reagent containers each having an opening; support portions which each hold a reagent container; and aspirating tubes which each aspirate a reagent in a reagent container. This analyzer includes a rotation mechanism which rotates each support portion toward the inner back side of the analyzer. Moreover, the support portion on which the reagent container is set is rotated toward the inner back side of the analyzer by a user. Accordingly, the reagent container is set, in a state where the position of the aspirating tube is aligned with the position of the reagent container. In this state, the aspirating tube is allowed to enter the reagent container, and the reagent is aspirated by the aspirating tube.

However, in the case of International Publication WO 2011/105247, as a result of the reagent container having been rotated by use of the rotation mechanism, the reagent container is set while being aligned with the aspiration position of the aspirating tube. Thus, the structure of the analyzer is complicated. Therefore, it is desired that the aspirating tube is allowed to enter the reagent container, with the position of the aspirating tube aligned with the position of the reagent container through a simpler configuration. On the other hand, it is desired, in replacing operation of a reagent container, to prevent a hand of a user from coming into contact with the aspirating tube, thereby to prevent contamination of the hand of the user and the aspirating tube.

SUMMARY OF THE INVENTION

The scope of the present invention is defined solely by the appended claims, and is not affected to any degree by the statements within this summary.

A first aspect of the present invention is a sample analyzer comprising: a reagent container setting part configured to install a reagent-container retainer for retaining a reagent container having an opening; an aspirating tube configured to aspirate a reagent in the reagent container; and an aspirating tube holder configured to hold the aspirating tube. The aspirating tube holder includes a cover, the cover having an open portion provided from a bottom face thereof to a side face thereof, the cover covering the aspirating tube with a region thereof other than the open portion. The aspirating tube holder includes a guide portion configured to guide the aspirating tube holder relative to the reagent-container retainer such that the aspirating tube holder is allowed to reach a state where the aspirating tube has entered the reagent container or a state where the aspirating tube has retreated from the reagent container.

A second aspect of the present invention is a sample analyzer comprising: a reagent container setting part configured to install a reagent container having an opening; an aspirating tube configured to aspirate a reagent in the reagent container; and an aspirating tube holder configured to hold the aspirating tube. The aspirating tube holder includes a cover, the cover having an open portion provided from a bottom face thereof to a side face thereof, the cover covering the aspirating tube with a region thereof other than the open portion. The aspirating tube holder includes a guide portion configured to guide the aspirating tube holder relative to the reagent container such that the aspirating tube holder is allowed to reach a state where the aspirating tube has entered the reagent container or a state where the aspirating tube has retreated from the reagent container.

A third aspect of the present invention is a reagent container for a sample analyzer, the sample analyzer comprising: an aspirating tube configured to aspirate a reagent; and an aspirating tube holder configured to hold the aspirating tube, wherein the aspirating tube holder includes a cover, the cover having an open portion provided from a bottom face thereof to a side face thereof, the cover covering the aspirating tube with a region thereof other than the open portion, the reagent container including: a reagent container body including an opening that allows the aspirating tube to enter; and a guided portion configured to allow the aspirating tube holder to be guided relative to the reagent container body such that the aspirating tube holder is allowed to reach a state where the aspirating tube has entered the reagent container body or a state where the aspirating tube has retreated from the reagent container body.

DETAILED DESCRIPTION OF THE PREFERRED EMBODIMENTS

Hereinafter, embodiments will be described with reference to the drawings.

First Embodiment

First, with reference to FIG. 1 to FIG. 20, a configuration of a sample analysis system 1 according to a first embodiment will be described.

Figure 1:
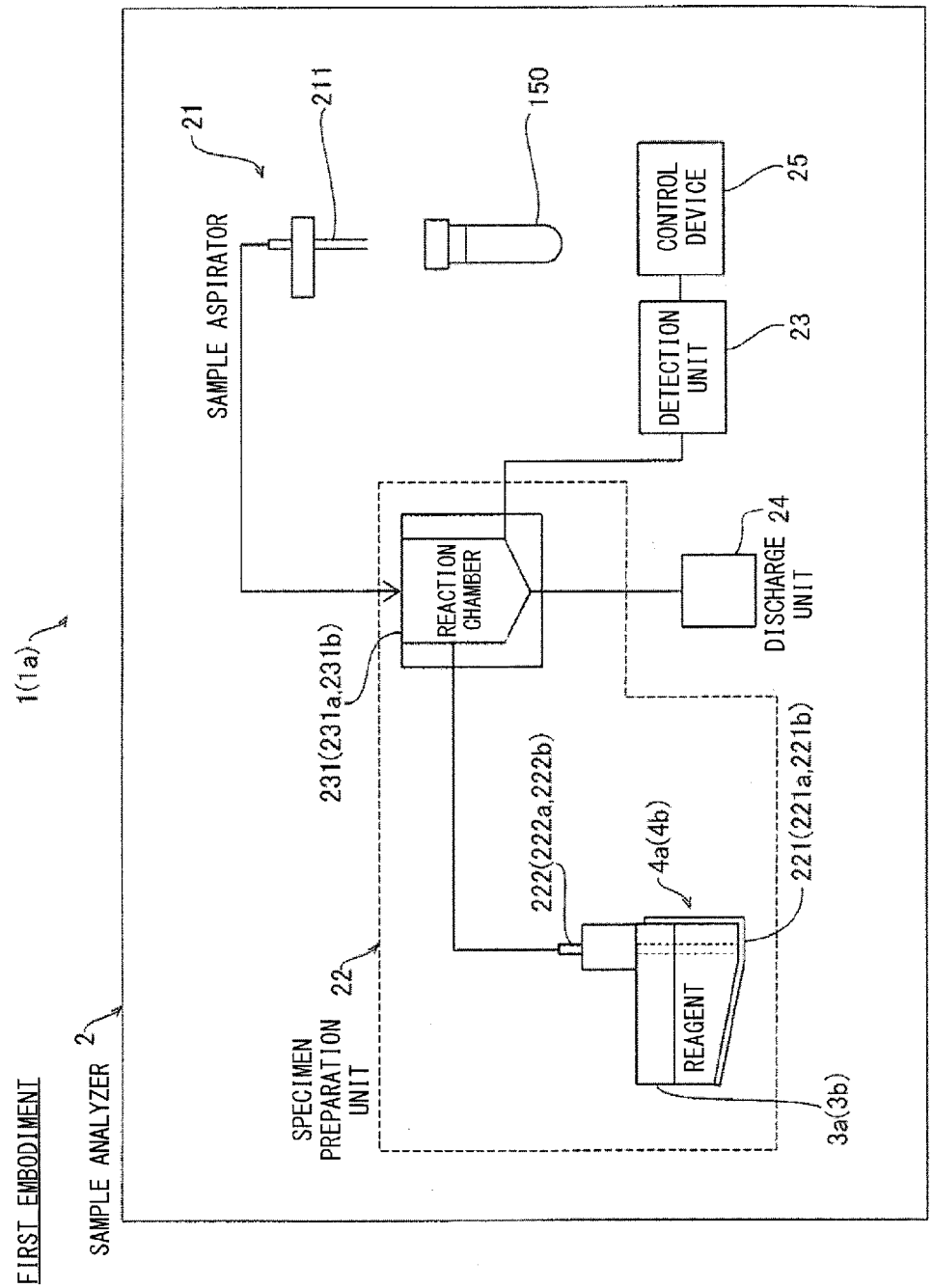
FIG. 1 is a schematic diagram showing a sample analysis system according to a first embodiment of the present invention.

As shown in FIG. 1, the sample analysis system 1 according to the first embodiment includes a sample analyzer 2, a first reagent container 3a to be used in performing white blood cell classification, a second reagent container 3b to be used in performing analysis of reticulocytes, a first reagent-container retainer 4a, and a second reagent-container retainer 4b.

The sample analyzer 2 measures blood which is a sample. Specifically, the sample analyzer 2 aspirates blood from a sample container 150 to prepare a detection specimen from the aspirated blood. Then, the sample analyzer 2 performs white blood cell classification and analysis of reticulocytes of blood from the detection specimen.

Figure 2:
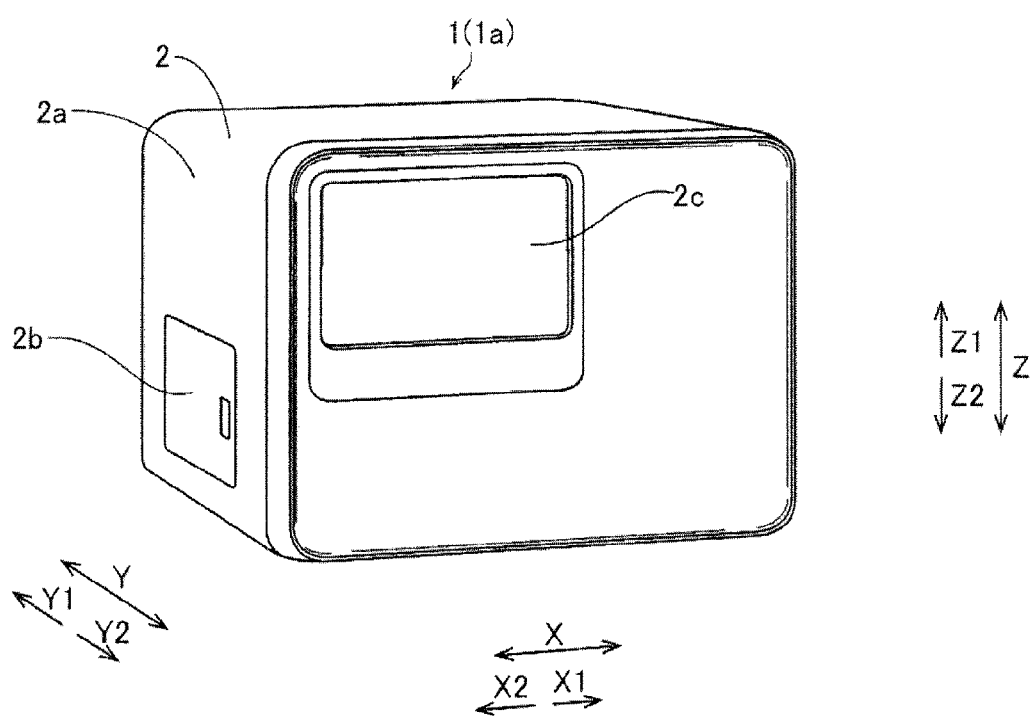
FIG. 2 is a perspective view showing an external appearance of the sample analysis system according to the first embodiment of the present invention.

As shown in FIG. 2, the outer shape of the body of the sample analyzer 2 is formed by a housing 2a. The sample analyzer 2 includes, on the left face of the housing 2a, a drawer part 2b for putting a reagent container setting part 221 (see FIG. 3) into/out of the housing 2a. Accordingly, it is possible to keep the reagent container setting part 221 inside the housing 2a when no reagent container is replaced as in normal use time. The sample analyzer 2 also includes a display portion 2c on the front face on a Y2 direction side of the housing 2a. The display portion 2c has a function of displaying information such as analysis results obtained through analysis performed by the sample analysis system 1. The Y2 direction is the forward direction of the sample analyzer 2. A Y1 direction is the rearward direction of the sample analyzer 2. The sample analyzer 2 will be described in detail later.

Figure 3:
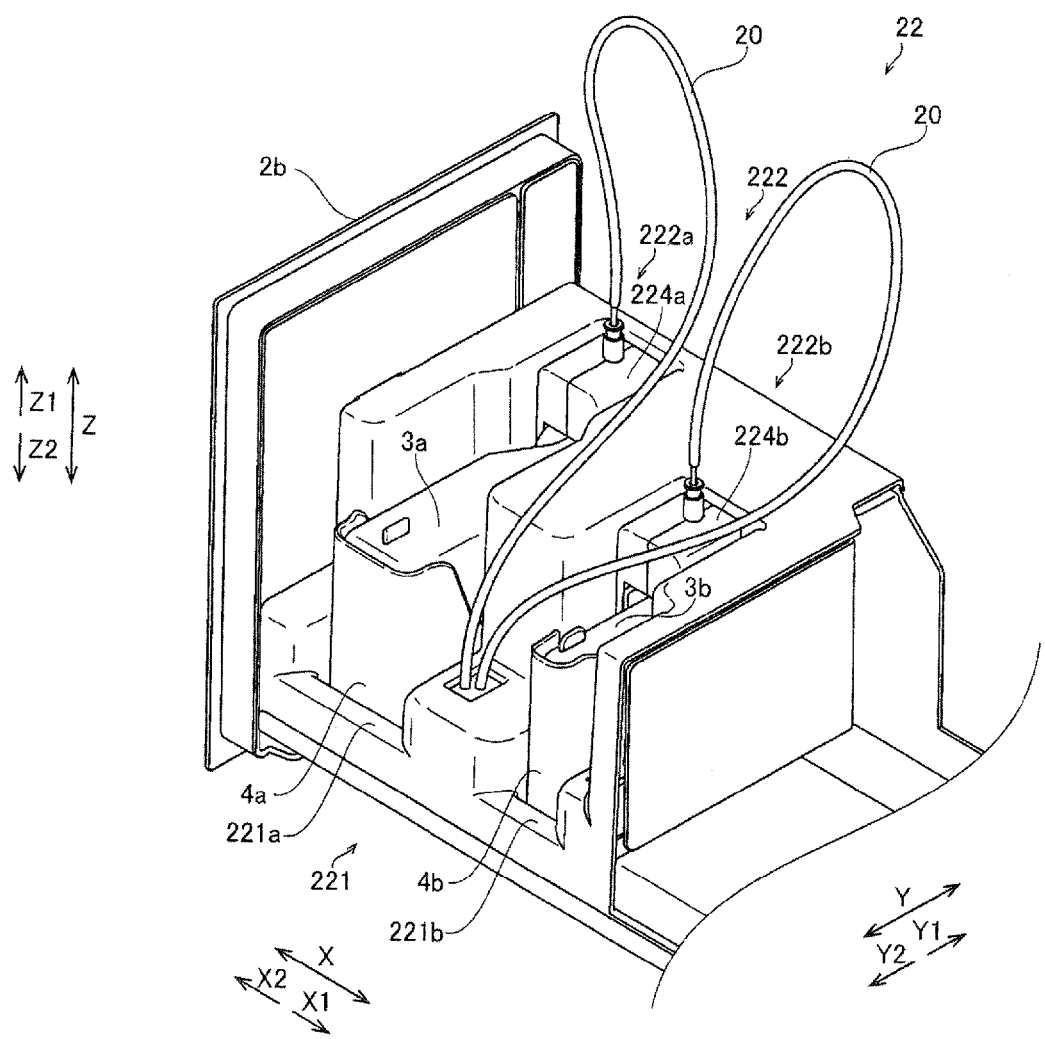
FIG. 3 is a perspective view showing a first reagent container setting part and a second reagent container setting part of the sample analysis system according to the first embodiment of the present invention.
Figure 4:
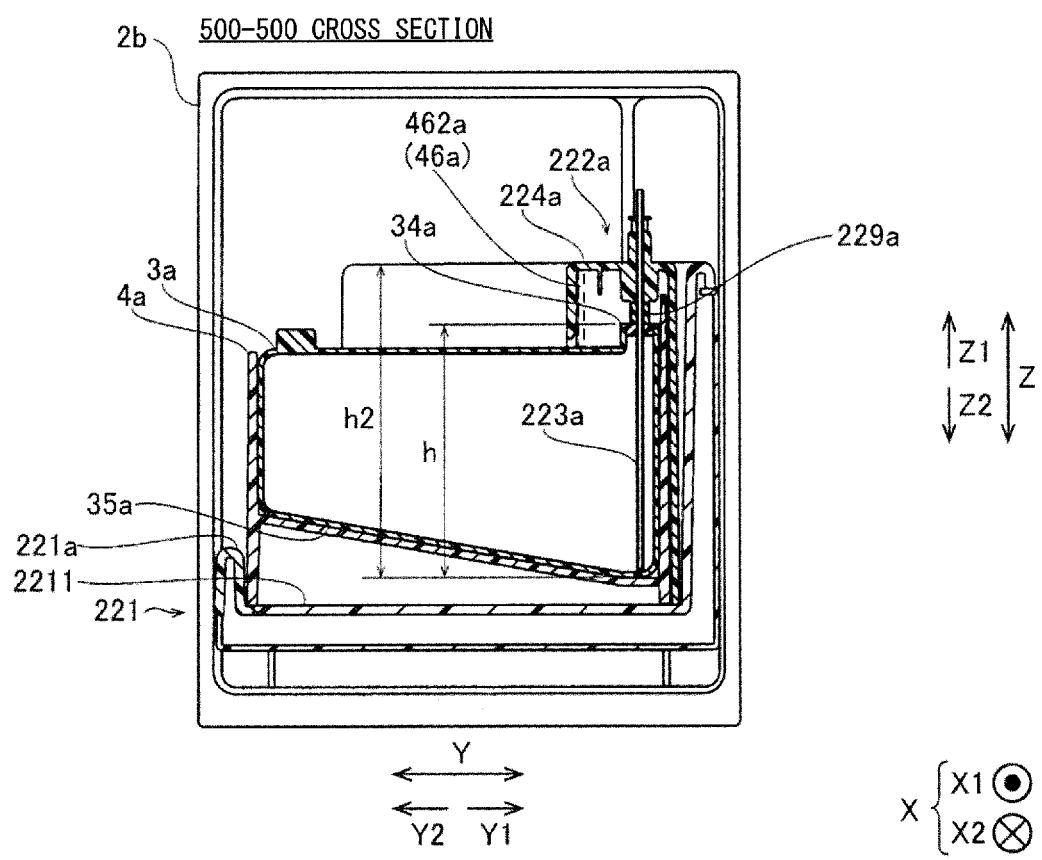
FIG. 4 is a cross-sectional view taken along a line 500-500 shown in FIG. 15.

As shown in FIG. 3, the reagent container setting part 221 includes a first reagent container setting part 221a in which to set the first reagent container 3a, and a second reagent container setting part 221b in which to set the second reagent container 3b. The first reagent container 3a is set in the first reagent container setting part 221a in a state of being retained in the first reagent-container retainer 4a. The second reagent container 3b is set in the second reagent container setting part 221b in a state of being retained in the second reagent-container retainer 4b. As shown in FIG. 4, the first reagent container setting part 221a includes a recessed portion 2211. The first reagent container setting part 221a is configured such that the first reagent-container retainer 4a retaining the first reagent container 3a is fitted in the recessed portion 2211. Similarly to the first reagent container setting part 221a, the second reagent container setting part 221b includes a recessed portion not shown. The second reagent container setting part 221b is configured such that the second reagent-container retainer 4b retaining the second reagent container 3b is fitted in the recessed portion. The first reagent container setting part 221a and the second reagent container setting part 221b will be described in detail later.

Next, configurations of the first reagent container 3a and the second reagent container 3b to be set in the sample analyzer 2 will be described in detail.

Figure 5:
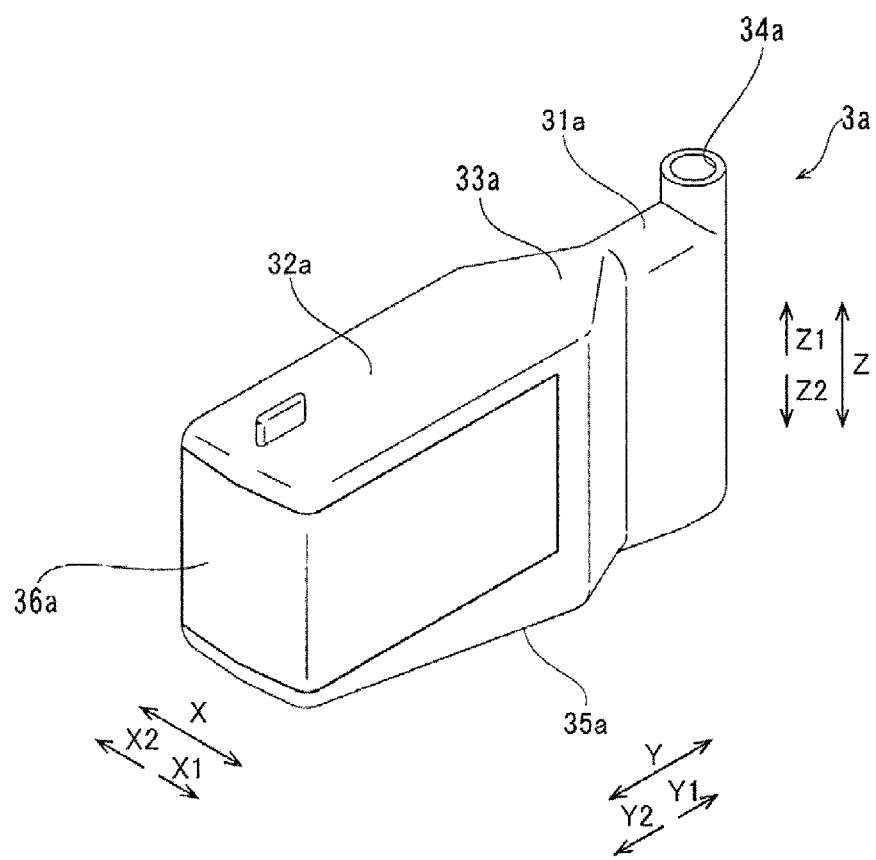
FIG. 5 is a perspective view of a first reagent container of the sample analysis system according to the first embodiment of the present invention.

As shown in FIG. 5, the first reagent container 3a contains a staining liquid which stains nucleic acids of white blood cells to be used in measurement for white blood cell classification. The first reagent container 3a includes a first portion 31a, a second portion 32a, a third portion 33a, an opening 34a, and a bottom portion 35a. To the first reagent container 3a, a label 36a indicating reagent information is attached so as to cover the side face on the Y2 side. A part of the label 36a is blue. The bottom portion 35a is formed so as to be inclined such that the Y1 side of the first reagent container 3a is lower than the Y2 side thereof.

Figure 6:
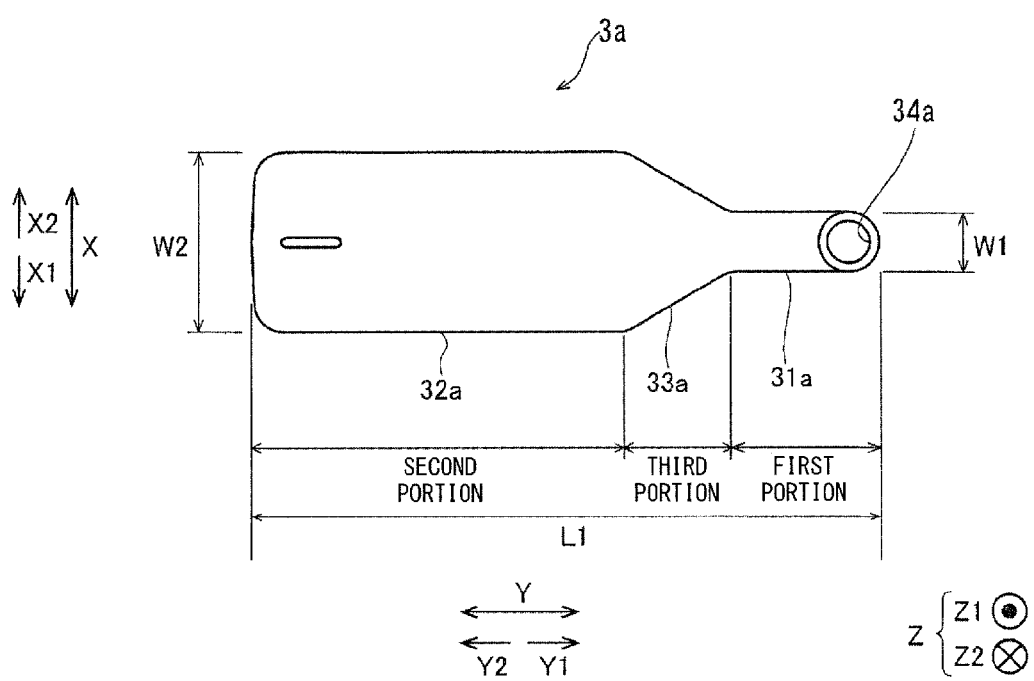
FIG. 6 is a plan view of the first reagent container of the sample analysis system according to the first embodiment of the present invention.

As shown in FIG. 6, the first portion 31a has a width W1 in an X direction. The second portion 32a has a width W2 greater than that of the first portion 31a. The third portion 33a is configured so as to connect the first portion 31a to the second portion 32a. The first portion 31a and the second portion 32a are formed in parallel in a Y direction. The first reagent container 3a has a length L1 in the Y direction.

The opening 34a is provided on a Z1 side of the first portion 31a. The opening 34a is provided near the end on the Y1 side of the first portion 31a. The Z1 direction is the upward direction of the sample analyzer 2. A Z2 direction is the downward direction of the sample analyzer 2.

Figure 7:
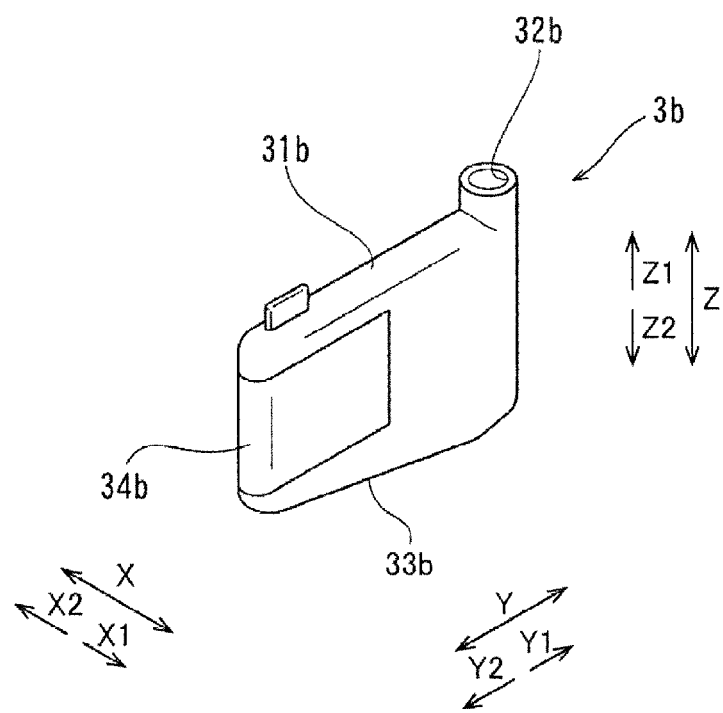
FIG. 7 is a perspective view of a second reagent container of the sample analysis system according to the first embodiment of the present invention.

As shown in FIG. 7, the second reagent container 3b contains a staining liquid which stains reticulocytes to be used in reticulocyte measurement. The second reagent container 3b includes a body portion 31b and an opening 32b. The body portion 31b includes a bottom portion 33b inclined such that the Y1 side thereof is lower than the Y2 side thereof. The second reagent container 3b has a shape different from that of the first reagent container 3a. To the second reagent container 3b, a label 34b indicating reagent information is attached so as to cover the side face on the Y2 side. A part of the label 34b is red.

Figure 8:
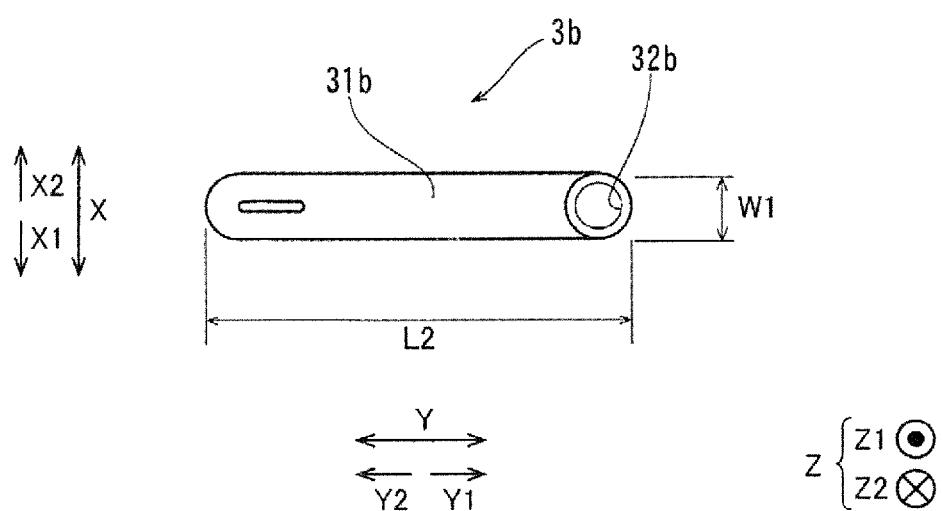
FIG. 8 is a plan view of the second reagent container of the sample analysis system according to the first embodiment of the present invention.

As shown in FIG. 8, the body portion 31b has, in the X direction, a width W1 which is substantially constant. That is, the body portion 31b has, in the X direction, a width that is substantially equal to the width W1 of the first portion 31a of the first reagent container 3a. The body portion 31b has a length L2 in the Y direction.

The opening 32b is provided on the Z1 side of the body portion 31b. The opening 32b is provided near the end on the Y1 side of the body portion 31b.

Next, configurations of the first reagent-container retainer 4a and the second reagent-container retainer 4b will be described in detail.

Figure 9:
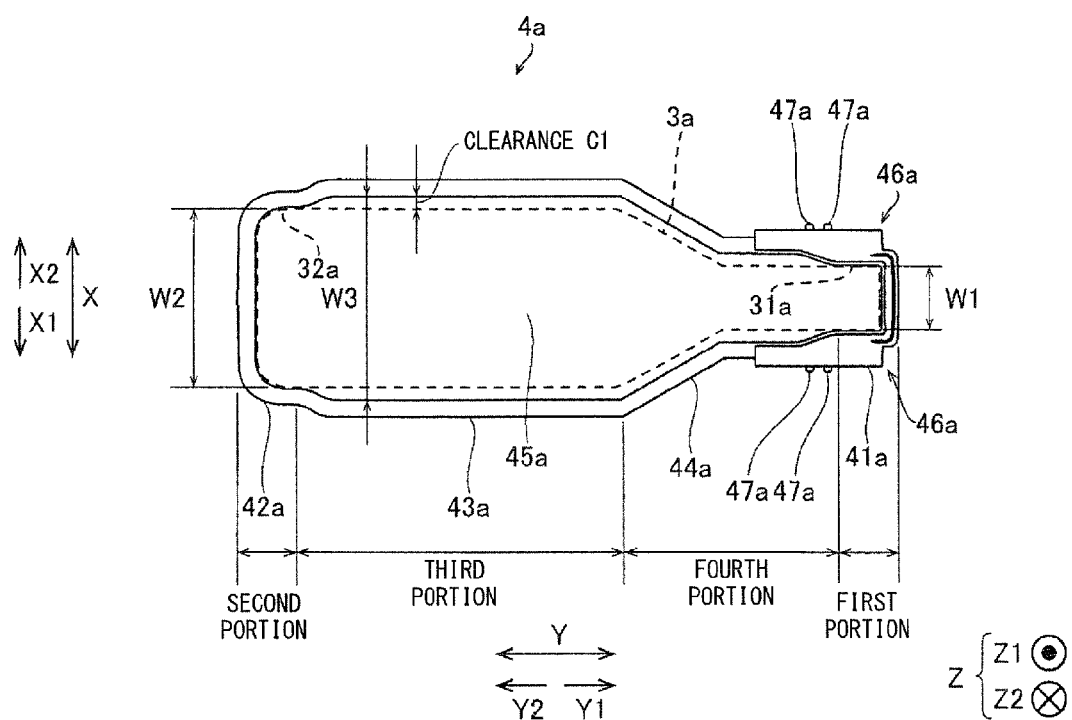
FIG. 9 is a plan view of a first reagent-container retainer of the sample analysis system according to the first embodiment of the present invention.
Figure 10:
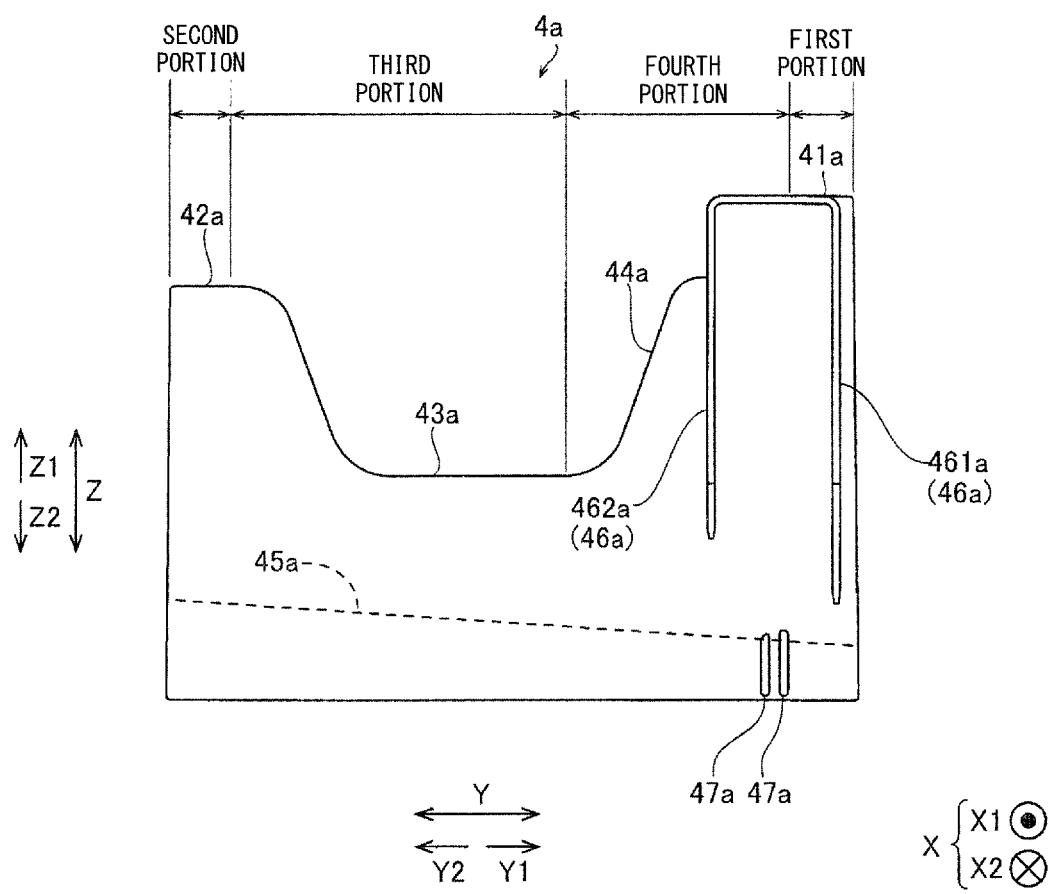
FIG. 10 is a side view of the first reagent-container retainer of the sample analysis system according to the first embodiment of the present invention.
Figure 11:
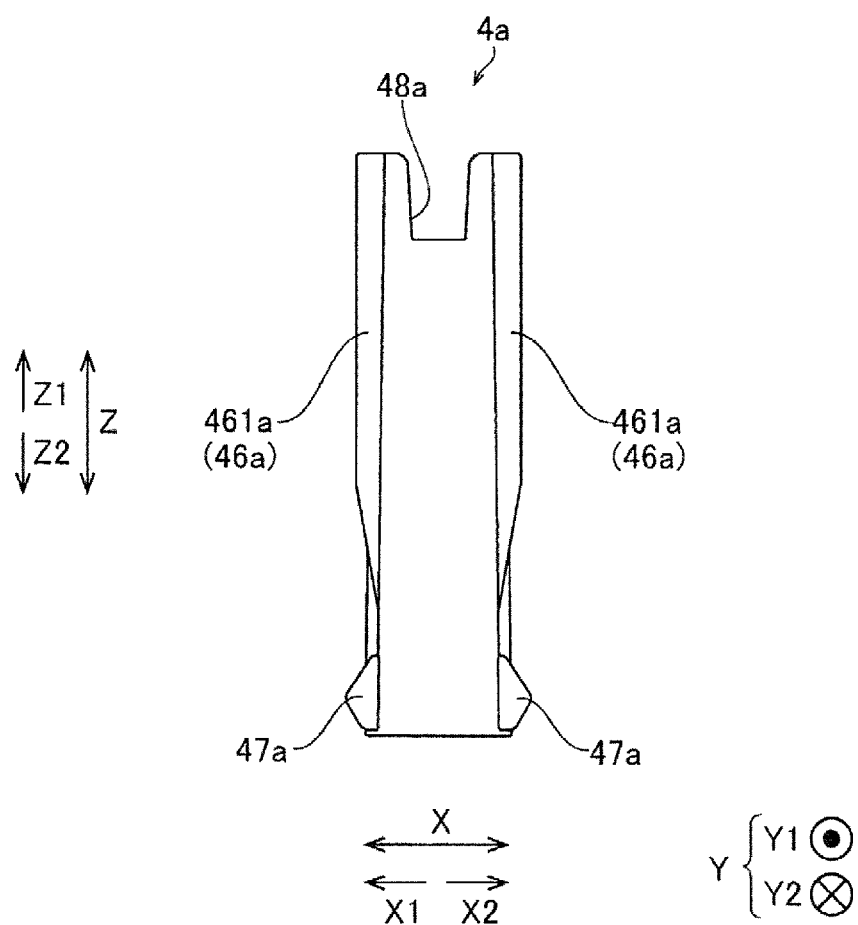
FIG. 11 is a view, seen from a Y1 side, of the first reagent-container retainer of the sample analysis system according to the first embodiment of the present invention.

As shown in FIG. 9, the first reagent-container retainer 4a is formed in a shape of a case having a bottom and an opening on the upper face thereof. The first reagent-container retainer 4a includes a first portion 41a, a second portion 42a, a third portion 43a, and a fourth portion 44a. As shown in FIG. 10, the first reagent-container retainer 4a includes a bottom portion 45a of a shape corresponding to that of the bottom portion 35a of the first reagent container 3a. The first reagent-container retainer 4a includes a guided portion 46a, and claws 47a formed near the lower end of the first reagent-container retainer 4a. As shown in FIG. 11, the first reagent-container retainer 4a includes a cutout 48a formed on the Z1 side of the first portion 41a.

As shown in FIG. 9, the first portion 41a is formed such that the width between its inner faces is W1 in the X direction. The second portion 42a is formed such that the width between its inner faces is W2 in the X direction. The third portion 43a is formed such that the maximum width between its inner faces is W3 in the X direction. The fourth portion 44a is formed so as to connect the first portion 41a to the third portion 43a. The width W2 of the second portion 42a is greater than the width W1 of the first portion 41a. The width W3 of the third portion 43a is greater than the width W2 of the second portion 42a.

The first portion 41a and the second portion 42a are configured so as to respectively sandwich the first portion 31a and the second portion 32a of the first reagent container 3a. The first reagent-container retainer 4a is formed such that, in the Y direction, the length between its inner faces is substantially the same as the length L1 of the first reagent container 3a. Accordingly, the first reagent-container retainer 4a fixes the first reagent container 3a in the X direction and the Y direction.

The first reagent-container retainer 4a is configured such that the side face of the first reagent container 3a retained in the first reagent-container retainer 4a has a clearance C1 with respect to the corresponding inner face of the third portion 43a and with respect to the corresponding inner face of the fourth portion 44a of the first reagent-container retainer 4a. Accordingly, even when the sample analysis system 1 is used in a place where the atmospheric pressure is low, and the first reagent container 3a has expanded in the X direction, the clearance C1 can absorb the expanded volume. In FIG. 9, the first reagent container 3a retained in the first reagent-container retainer 4a is indicated by a dotted line.

As shown in FIG. 10, the guided portion 46a is configured to guide an aspirating tube holder 224a relative to the first reagent container 3a such that the aspirating tube holder 224a is allowed to reach a state where an aspirating tube 223a described later has entered the first reagent container 3a or a state where the aspirating tube 223a has retreated from the first reagent container 3a. The guided portion 46a is configured by two guided rails 461a and two guided rails 462a. The guided rails 461a are provided on the outer faces on the X1 side and the X2 side of the first portion 41a, respectively. The guided rails 462a are provided on the outer faces on the X1 side and the X2 side of the fourth portion 44a, respectively. The guided rails 461a and 462a are each formed in a straight line extending in the Z direction. The guided rails 461a and 462a are formed so as to be substantially parallel to each other. The lower end of each guided rail 461a is located below the lower end of each guided rail 462a. The upper end of each of the guided rails 461a and 462a is provided above the opening 34a (see FIG. 4) of the first reagent container 3a retained in the first reagent-container retainer 4a. By means of the guided portion 46a, through simple configuration, it is possible to align the position of the aspirating tube 223a with the position of the opening 34a of the first reagent container 3a, thereby to accurately cause the aspirating tube 223a to enter the opening 34a of the first reagent container 3a.

Figure 12:
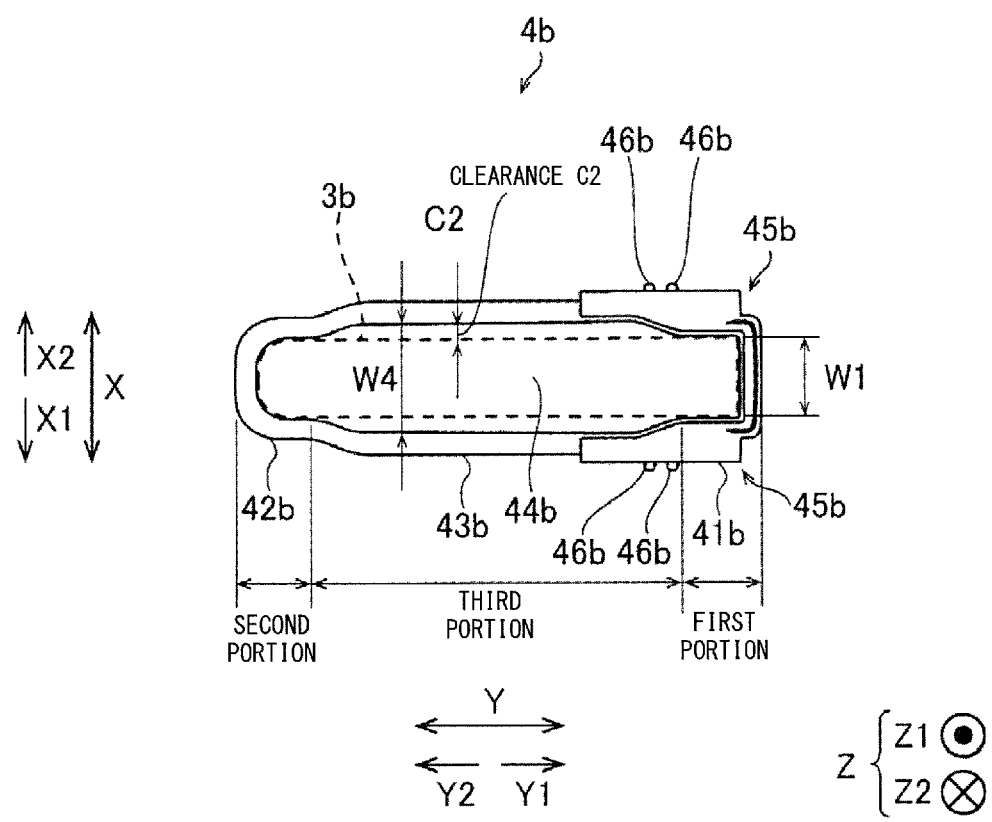
FIG. 12 is a plan view of a second reagent-container retainer of the sample analysis system according to the first embodiment of the present invention.
Figure 13:
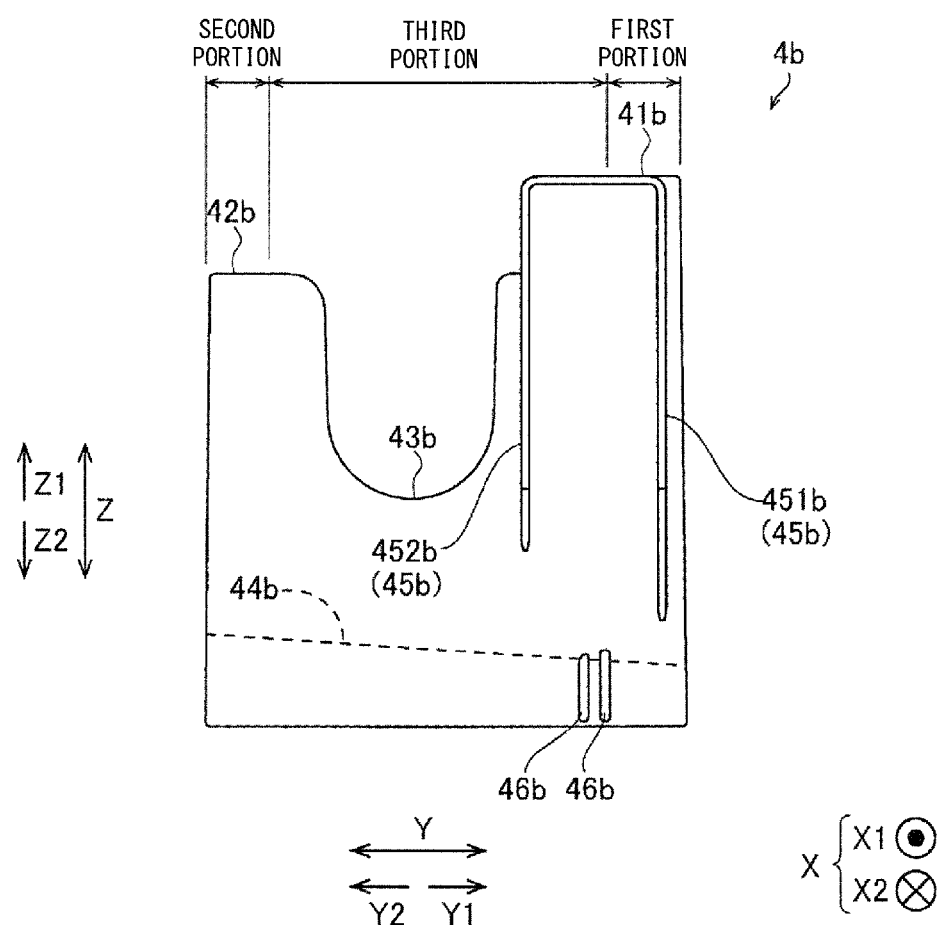
FIG. 13 is a side view of the second reagent-container retainer of the sample analysis system according to the first embodiment of the present invention.
Figure 14:
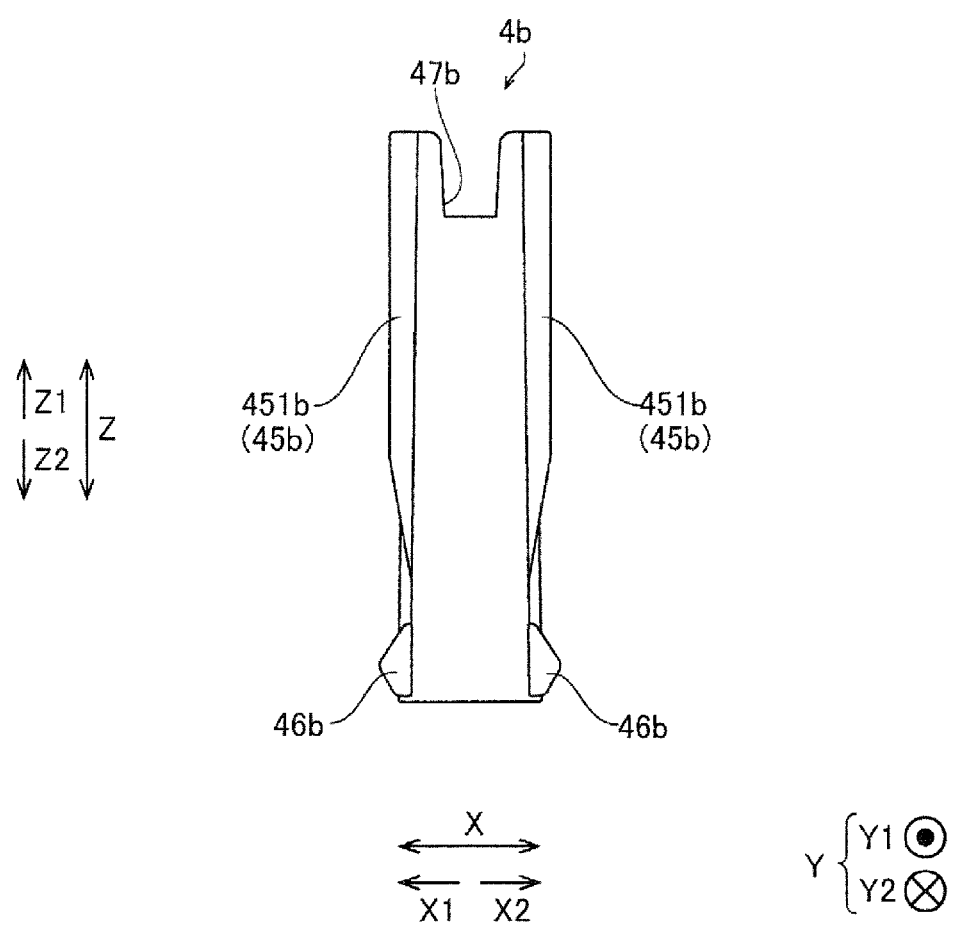
FIG. 14 is a view, seen from the Y1 side, of the second reagent-container retainer of the sample analysis system according to the first embodiment of the present invention.

As shown in FIG. 12, the second reagent-container retainer 4b is formed in a shape of a case having a bottom and an opening on the upper face thereof. The second reagent-container retainer 4b includes a first portion 41b, a second portion 42b, and a third portion 43b. As shown in FIG. 13, the second reagent-container retainer 4b includes a bottom portion 44b of a shape corresponding to that of the bottom portion 33b of the second reagent container 3b. The second reagent-container retainer 4b includes a guided portion 45b and claws 46b formed near the lower end of the first portion 41b. As shown in FIG. 14, the second reagent-container retainer 4b includes a cutout 47b on the Z1 side of the first portion 41b.

As shown in FIG. 12, the first portion 41b is formed such that the width between its inner faces is W1 in the X direction. The second portion 42b is formed such that the width between its inner faces is W1. The third portion 43b is formed such that the maximum width between its inner faces is W4. The width W4 of the third portion 43b is greater than the width W1 of the first portion 41b and the second portion 42b.

The first portion 41b and the second portion 42b are configured so as to sandwich the body portion 31b of the second reagent container 3b. The second reagent-container retainer 4b has a length between its inner faces, in the Y direction, that is substantially the same as the length L2 of the second reagent container 3b. Accordingly, the second reagent-container retainer 4b fixes the second reagent container 3b in the X direction and the Y direction.

The second reagent-container retainer 4b is configured such that the side face of the second reagent container 3b retained in the second reagent-container retainer 4b has a clearance C2 with respect to the corresponding inner face of the third portion 43b of the second reagent-container retainer 4b. Accordingly, even when the sample analysis system 1 is used in a place where the atmospheric pressure is low, and the second reagent container 3b has expanded in the X direction, the clearance C2 can absorb the expanded volume. In FIG. 12, the second reagent container 3b retained in the second reagent-container retainer 4b is indicated by a dotted line.

The guided portion 45b is configured to guide an aspirating tube holder 224b relative to the second reagent container 3b such that the aspirating tube holder 224b is allowed to reach a state where an aspirating tube 223b described later has entered the second reagent container 3b or a state where the aspirating tube 223b has retreated from the second reagent container 3b. As shown in FIG. 13, the guided portion 45b is configured by two guided rails 451b and two guided rails 452b. The guided rails 451b are provided on the outer faces on the X1 side and the X2 side of the first portion 41b, respectively. The guided rails 452b are provided on the outer faces on the X1 side and the X2 side of the third portion 43b, respectively. The guided rails 451b and 452b are each formed in a straight line extending in the Z direction. The guided rails 451b and 452b are formed so as to be substantially parallel to each other. The lower end of each guided rail 451b is located below the lower end of each guided rail 452b. Similarly to the upper end of each of the guided rails 461a and 462a of the first reagent-container retainer 4a being provided above the opening 34a of the first reagent container 3a retained in the first reagent-container retainer 4a, the upper end of each of the guided rails 451b and 452b is provided above the opening 32b of the second reagent container 3b retained in the second reagent-container retainer 4b. By means of the guided portion 45b, through simple configuration, it is possible to align the position of the aspirating tube 223b with the position of the opening 32b of the second reagent container 3b, thereby to accurately cause the aspirating tube 223b to enter the opening 32b of the second reagent container 3b.

Next, a configuration of the sample analyzer 2 will be described in detail.

As shown in FIG. 1, the sample analyzer 2 includes a sample aspirator 21, a specimen preparation unit 22, a detection unit 23, a discharge unit 24, and a control device 25.

The sample aspirator 21 is configured to aspirate blood from a sample container 150 by means of a sample aspirating tube 211, to discharge the aspirated blood into a reaction chamber 231 through a flow path.

The specimen preparation unit 22 mainly includes the reagent container setting part 221, a reagent aspirator 222, and the reaction chamber 231. It should be noted that the reagent container setting part 221 includes the first reagent container setting part 221a and the second reagent container setting part 221b, and the reaction chamber 231 includes reaction chambers 231a and 231b, but FIG. 1 is shown in a simplified manner.

Figure 15:
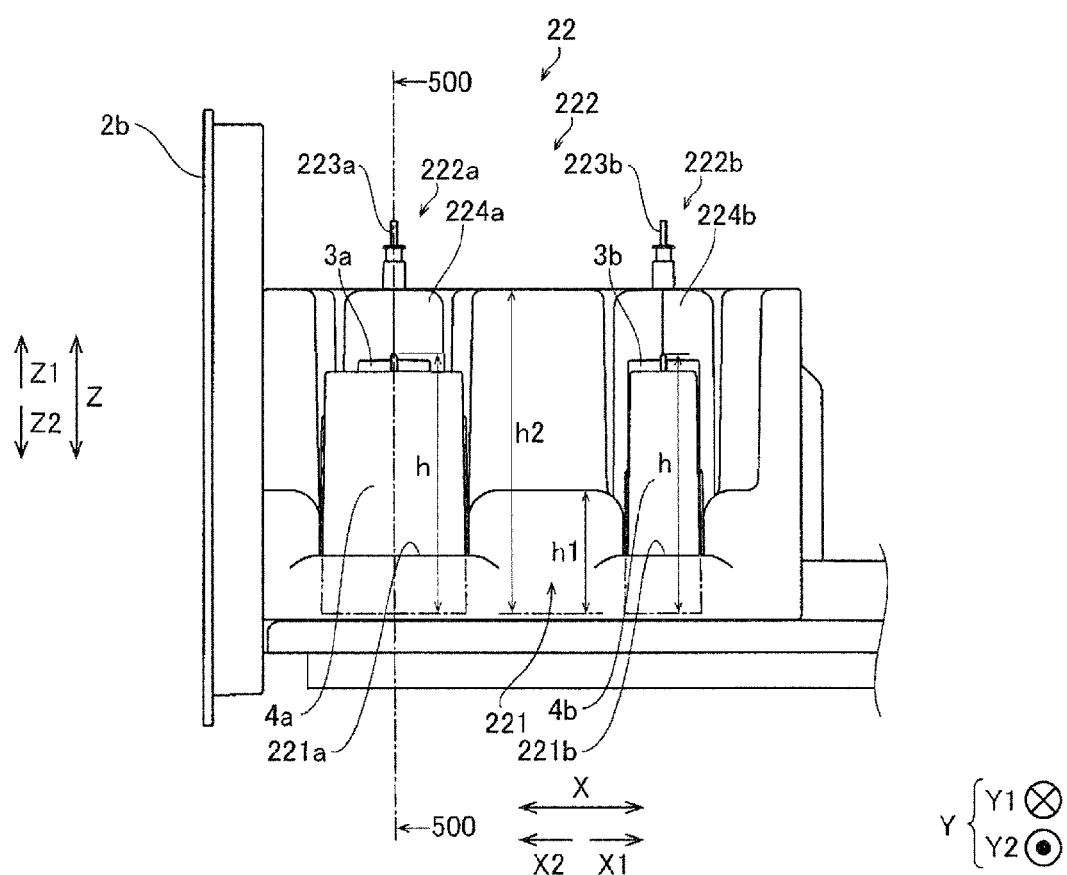
FIG. 15 is a view, seen from a Y2 side, of the first reagent container setting part and the second reagent container setting part of the sample analysis system according to the first embodiment of the present invention.

As shown in FIG. 15, the first reagent container setting part 221a is configured such that a height h1 at the upper end thereof on the Y2 side being the reagent-container-removing side is equal to or smaller than a half of a height h at the upper end of the first reagent container 3a when the first reagent container 3a is set in the first reagent container setting part 221a. Accordingly, the first reagent container setting part 221a allows the first reagent container 3a to be exposed on the Y2 side. Moreover, in the first reagent container setting part 221a, a height h2 at the upper end of regions, of the inner wall face of the first reagent container setting part 221a, that extend from a middle portion thereof toward the Y1 side is greater than the height h at the upper end of the first reagent container 3a when the first reagent container 3a is set in the first reagent container setting part 221a. Accordingly, it is possible to set the first reagent container 3a in the first reagent-container retainer 4a in a more stable manner. In addition, the first reagent container setting part 221a is configured such that the first reagent container 3a to which the aspirating tube holder 224a has been mounted can be set at a predetermined position without falling down. The reference position for the heights is the lowest position in the first reagent container 3a set in the first reagent container setting part 221a.

Similarly, the second reagent container setting part 221b is configured such that the height h1 on the Y2 side being the reagent-container-removing side is equal to or smaller than a half of the height h of the second reagent container 3b when the second reagent container 3b is set in the second reagent container setting part 221b. Accordingly, the second reagent container setting part 221b allows the second reagent container 3b to be exposed on the Y2 side. Moreover, in the second reagent container setting part 221b, the height h2 of regions, of the inner wall face of the second reagent container setting part 221b, that extend from a middle portion thereof toward the Y1 side is greater than the height h of the second reagent container 3b when the second reagent container 3b is set in the second reagent container setting part 221b. In addition, the second reagent container setting part 221b is configured such that the second reagent container 3b to which the aspirating tube holder 224b has been mounted can be set at a predetermined position without falling down.

Figure 16:
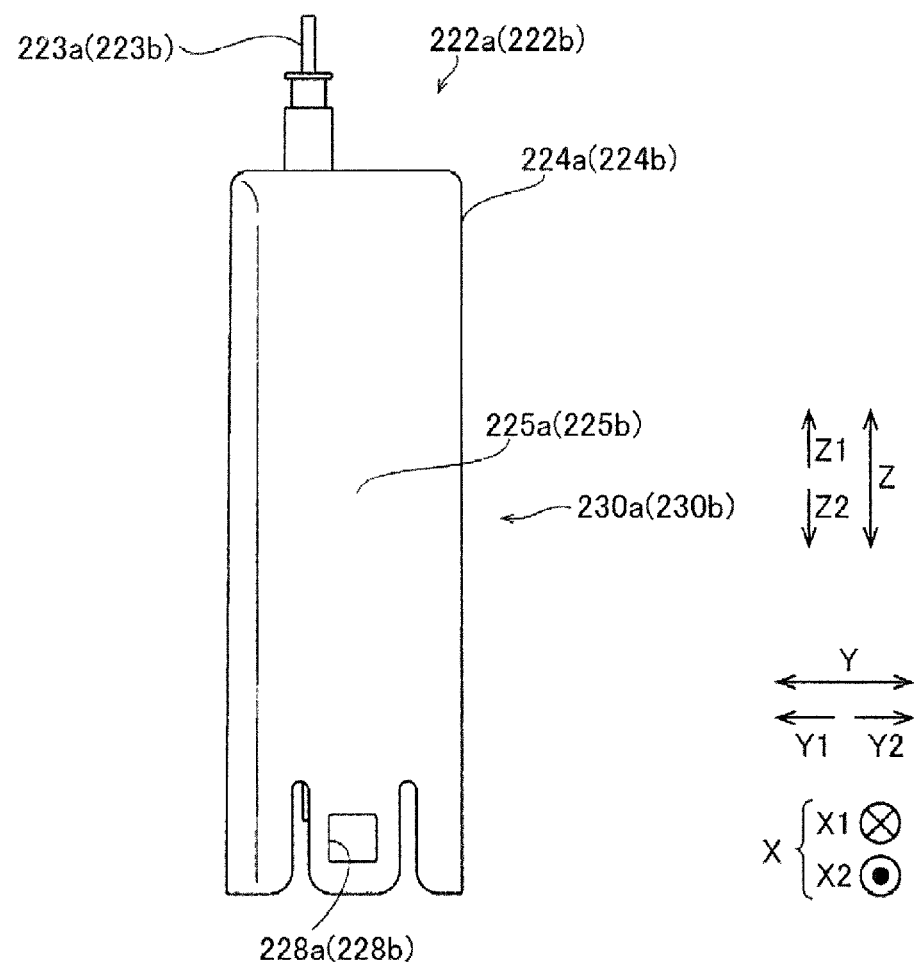
FIG. 16 is a view, seen from an X2 side, of a reagent aspirator of the sample analysis system according to the first embodiment of the present invention.

As shown in FIG. 16, the reagent aspirator 222 is configured by a reagent aspirator 222a which aspirates a reagent from the first reagent container 3a, and a reagent aspirator 222b which aspirates a reagent from the second reagent container 3b.

Figure 17:
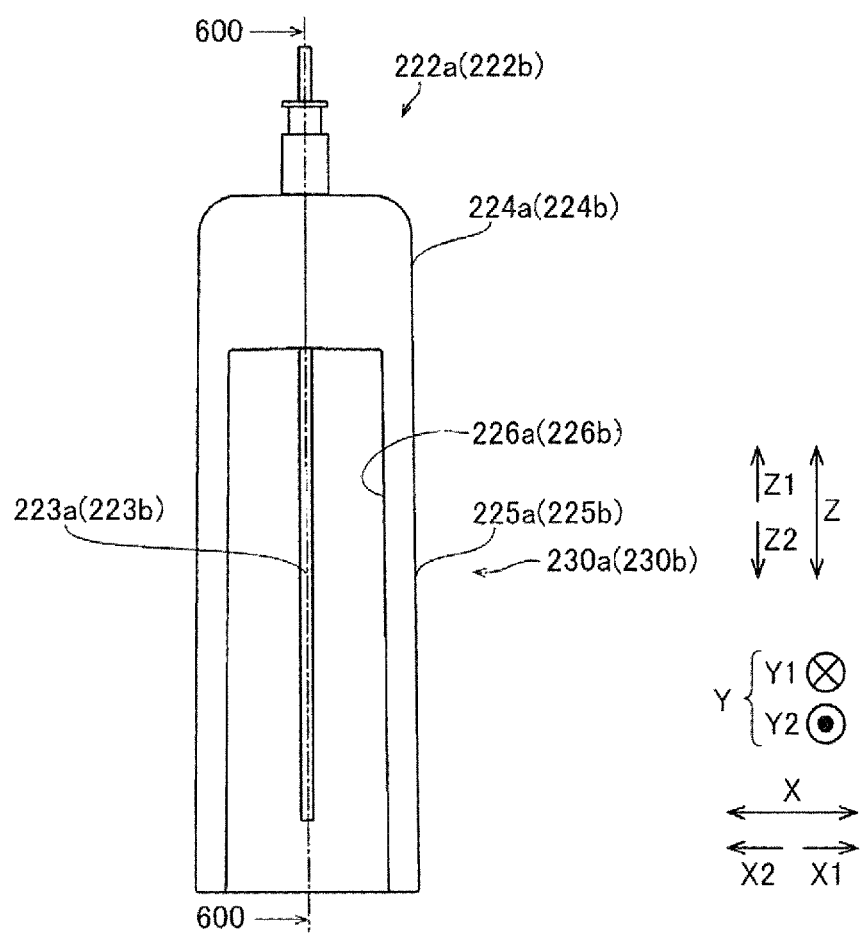
FIG. 17 is a view, seen from the Y2 side, of the reagent aspirator of the sample analysis system according to the first embodiment of the present invention.
Figure 18:
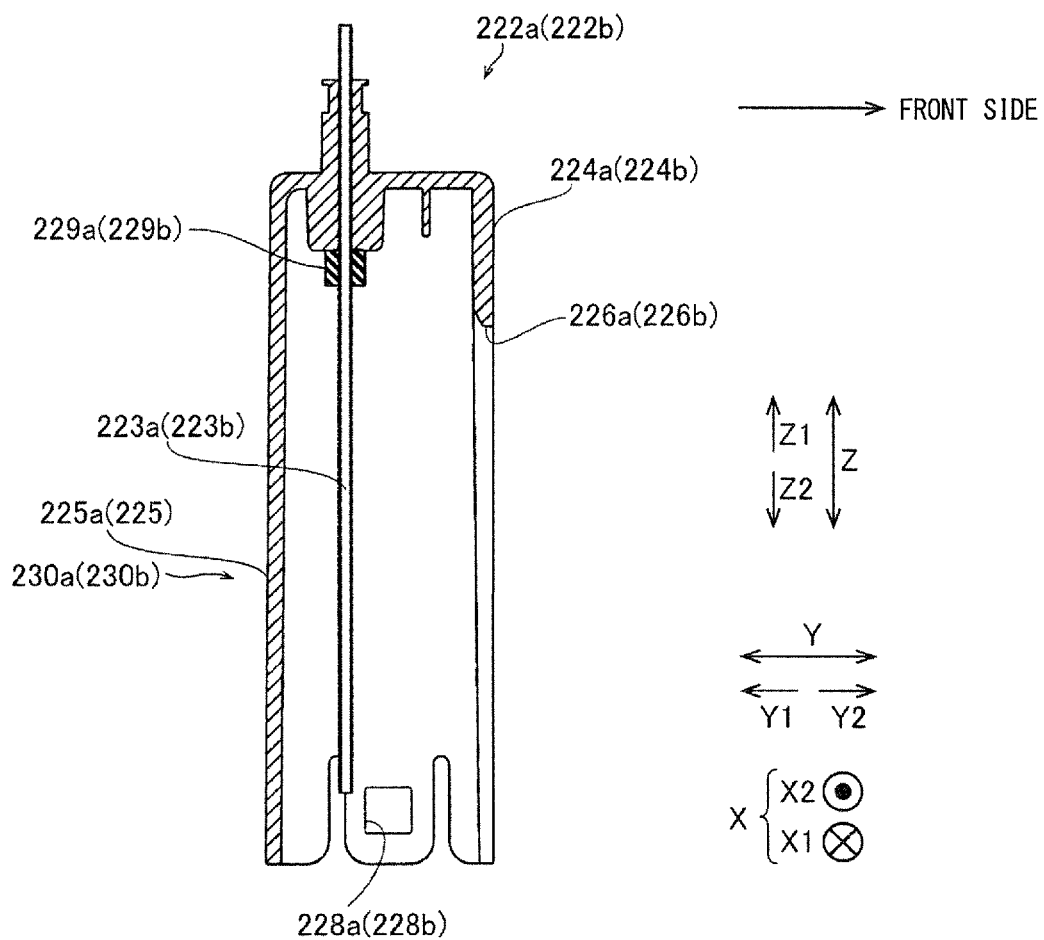
FIG. 18 is a cross-sectional view taken along a line 600-600 shown in FIG. 17.

As shown in FIG. 17, the reagent aspirator 222a includes the aspirating tube 223a, the aspirating tube holder 224a, side faces 225a, an open portion 226a, and guide portions 227a (see FIG. 19) to be engaged with the guided rails 461a and 462a. Side faces 225a other than that on the Y2 side function as a cover portion 230a which covers the sides of the aspirating tube 223a. By means of the cover portion 230a, it is possible to prevent a hand of the user from coming into contact with the aspirating tube 223a. As shown in FIG. 18, the aspirating tube holder 224a includes a hole 228a to be fitted with the claws 47a, and a packing 229a provided below the portion that holds the aspirating tube 223a.

Similarly to the reagent aspirator 222a, as shown in FIG. 17, the reagent aspirator 222b includes the aspirating tube 223b, the aspirating tube holder 224b, side faces 225b, an open portion 226b, and guide portions 227b (see FIG. 19) to be engaged with the guided rails 451b and 452b. Side faces 225b other than that on the Y2 side function as a cover portion 230b which covers the sides of the aspirating tube 223b. By means of the cover portion 230b, it is possible to prevent a hand of the user from coming into contact with the aspirating tube 223b. As shown in FIG. 18, the aspirating tube holder 224b includes a hole 228b to be fitted with the claws 46b, and a packing 229b provided below the portion that holds the aspirating tube 223b. In addition, the aspirating tube holder 224a is blue. The aspirating tube holder 224b is red. The color of the aspirating tube holder 224a is the same (blue) as the color of a part of the reagent indicating label of the first reagent container 3a. The color of the aspirating tube holder 224b is the same (red) as the color of a part of the reagent indicating label of the second reagent container 3b. Accordingly, it is possible to visually confirm the accordance between the aspirating tube holder 224a and its corresponding first reagent container 3a, or the accordance between the aspirating tube holder 224b and its corresponding second reagent container 3b. It should be noted that the aspirating tube 223a of the reagent aspirator 222a and the aspirating tube 223b of the reagent aspirator 222b are connected to the reaction chamber 231a and the reaction chamber 231b via tubes 20 (see FIG. 3), respectively. The tubes 20 have lengths that allow the reagent aspirators 222a and 222b to be easily taken out of the first reagent-container retainer 4a and the second reagent-container retainer 4b, respectively.

The aspirating tube holders 224a and 224b are formed from resin that allows radio waves pass therethrough. The reagent aspirators 222a and 222b have similar configurations except that the colors of the aspirating tube holders 224a and 224b are different. Therefore, in the following, only the reagent aspirator 222a will be described, and description of the reagent aspirator 222b will be omitted.

As shown in FIG. 17, the aspirating tube 223a is configured to aspirate a reagent in the first reagent container 3a. The aspirating tube 223a is formed so as to extend in the Z direction. The aspirating tube 223a has a length that reaches the vicinity of the deepest portion of the first reagent container 3a (see FIG. 4).

The aspirating tube holder 224a is formed in a substantially rectangular parallelepiped shape. Inside the aspirating tube holder 224a, a cavity of a substantially rectangular parallelepiped shape is formed. The aspirating tube holder 224a is configured to hold the aspirating tube 223a.

The open portion 226a is provided in the side face 225a on the Y2 side of the aspirating tube holder 224a. Specifically, the open portion 226a is provided in the side face 225a on the Y2 side, in a state where the first reagent container 3a to which the aspirating tube holder 224a has been mounted is set in the first reagent container setting part 221a. Thus, it is possible to visually confirm the aspirating tube 223a through the open portion 226a, and thus, it is possible to visually confirm that the aspirating tube 223a has been caused to enter the opening 34a of the first reagent container 3a by means of the guided portion 46a.

Figure 19:
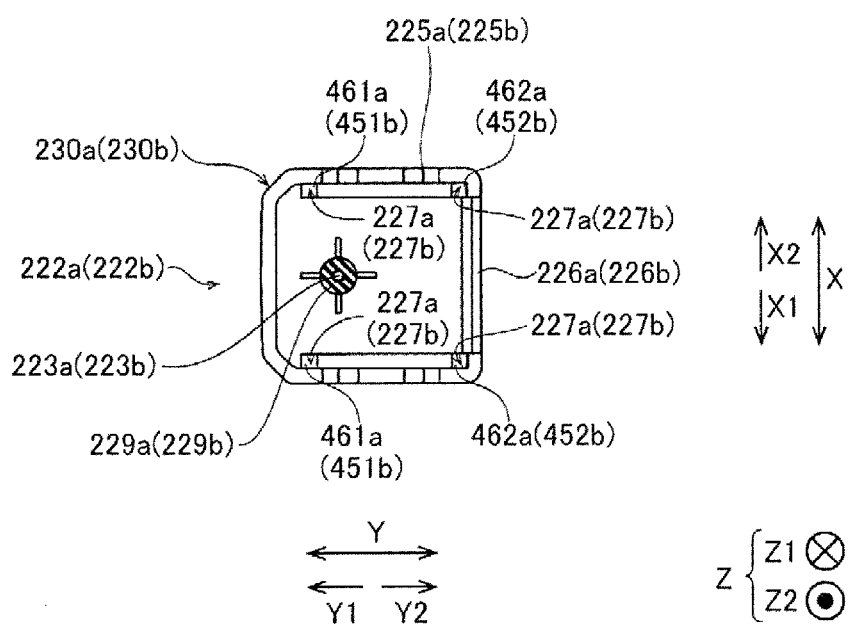
FIG. 19 is a view, seen from a Z2 side, of the reagent aspirator of the sample analysis system according to the first embodiment of the present invention.

As shown in FIG. 19, the guide portions 227a have a function of being engaged with the guided rails 461a and 462a to allow the aspirating tube holder 224a to linearly move in a sliding manner. In addition, the guide portions 227a are formed by portions, that are to come into contact with the guided rails 461a and 462a, of the side faces 225a of the aspirating tube holder 224a. The guide portions 227a are provided on each of the X1 side and the X2 side. The guide portions 227a are provided on each of the Y1 side and the Y2 side. The guide portions 227a are formed so as to linearly extend along the Z direction. The guide portions 227a on the Y2 side are configured to be engaged with the guided rails 462a. The guide portions 227a on the Y1 side are configured to be engaged with the guided rails 461a. The guide portions 227a of the aspirating tube holder 224a are configured to, when they are to be engaged with the guided rails 461a and 462a, start to be engaged with the guided rails 461a and 462a of the first reagent-container retainer 4a, at a position on the first reagent container 3a side relative to the leading end on the Z1 side of the aspirating tube 223a. Accordingly, when the guided portion 46a of the first reagent-container retainer 4a is to be engaged with the guide portions 227a of the aspirating tube holder 224a, it is possible to prevent the leading end of the aspirating tube 223a from coming into contact with the first reagent-container retainer 4a. The guide portions 227a are formed in shapes that can be engaged with each of the guided portion 46a of the first reagent container 3a and the guided portion 45b of the second reagent container 3b. Accordingly, it is possible to reduce the kinds of parts at the time of production of the sample analysis system 1.

By the claws 47a of the first reagent-container retainer 4a being fitted into the hole 228a, the aspirating tube holder 224a is set in the first reagent-container retainer 4a retaining the first reagent container 3a.

As shown in FIG. 1, the reaction chamber 231 includes the reaction chamber 231a in which a specimen for white blood cell classification is prepared, and the reaction chamber 231b in which a specimen for reticulocytes analysis is prepared. The reaction chamber 231a is configured to heat a mixed solution of a sample and a reagent for white blood cell classification at a predetermined temperature. The reaction chamber 231b is configured to heat a mixed solution of a sample and a reagent for reticulocytes at a predetermined temperature.

The detection unit 23 has a function of measuring, through flow cytometry, detection specimens sent from the reaction chambers 231a and 231b. Detection results obtained by the detection unit 23 are transmitted to the control device 25. When the detection process ends, the detection specimens sent to the detection unit 23 is sent to the discharge unit 24.

The discharge unit 24 is configured to discharge specimens having been subjected to measurement.

The control device 25 is implemented by a personal computer, and includes a CPU, a storage section, and the like. The control device 25 analyzes measurement data transmitted from the detection unit 23, and generates analysis results regarding white blood cell classification and reticulocytes.

Figure 20:
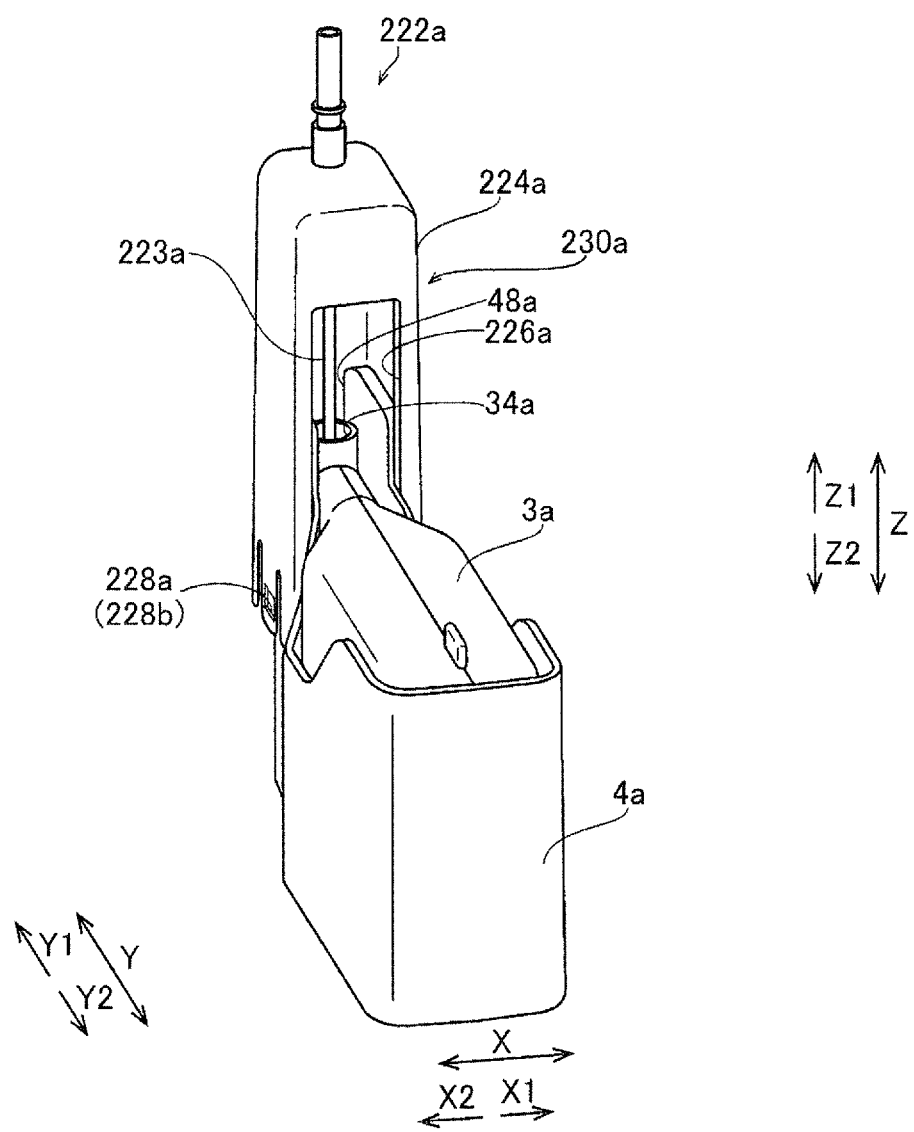
FIG. 20 is a diagram for explaining operation of mounting the reagent aspirator to the first reagent container set in the first reagent container setting part of the sample analysis system according to the first embodiment of the present invention.

Next, with reference to FIG. 3 and FIG. 20, a method for setting the first reagent container 3a and the second reagent container 3b to the sample analyzer 2. The method for setting the second reagent container 3b is the same as the method for setting the first reagent container 3a. Thus, only the method for setting the first reagent container 3a is described here, and description of the method for setting the second reagent container 3b is omitted.

First, as shown in FIG. 20, the first reagent container 3a is set in the first reagent-container retainer 4a.

Next, the reagent aspirator 222a is mounted to the first reagent-container retainer 4a in which the first reagent container 3a has been set. At this time, the guide portions 227a of the aspirating tube holder 224a start to be engaged with the guided rails 461a and 462a of the first reagent-container retainer 4a at a position on the first reagent container 3a side relative to the position of the leading end of the aspirating tube 223a. By means of the cutout 48a in the first reagent-container retainer 4a, it is possible to prevent the aspirating tube 223a from coming into contact with the first reagent-container retainer 4a.

In this state, the aspirating tube holder 224a is moved toward the Z2 side. Accordingly, mounting of the reagent aspirator 222a to the first reagent-container retainer 4a in which the first reagent container 3a has been set is completed. At this time, by the claws 47a of the first reagent-container retainer 4a being fitted into the hole 228a, the aspirating tube holder 224a is fixedly set in the first reagent-container retainer 4a retaining the first reagent container 3a.

Next, as shown in FIG. 3, the first reagent-container retainer 4a in which the first reagent container 3a is retained and the reagent aspirator 222a has been set is disposed in the first reagent container setting part 221a. Through the setting operation above, the first reagent container 3a is set in the sample analyzer 2.

Second Embodiment

In the following, with reference to FIG. 21 to FIG. 25, a configuration of a sample analysis system 1a according to a second embodiment will be described.

In the second embodiment, the sample analysis system 1a will be described in which a first reagent container 303a and a second reagent container 303b are directly set in the first reagent container setting part 221a and the second reagent container setting part 221b, which is different from the first embodiment in which the first reagent container 3a and the second reagent container 3b are respectively retained in the first reagent-container retainer 4a and the second reagent-container retainer 4b and then are set in the sample analyzer 2. It should be noted that similar configurations to those in the first embodiment above are denoted by the same reference characters, and description thereof will be omitted.

Figure 21:
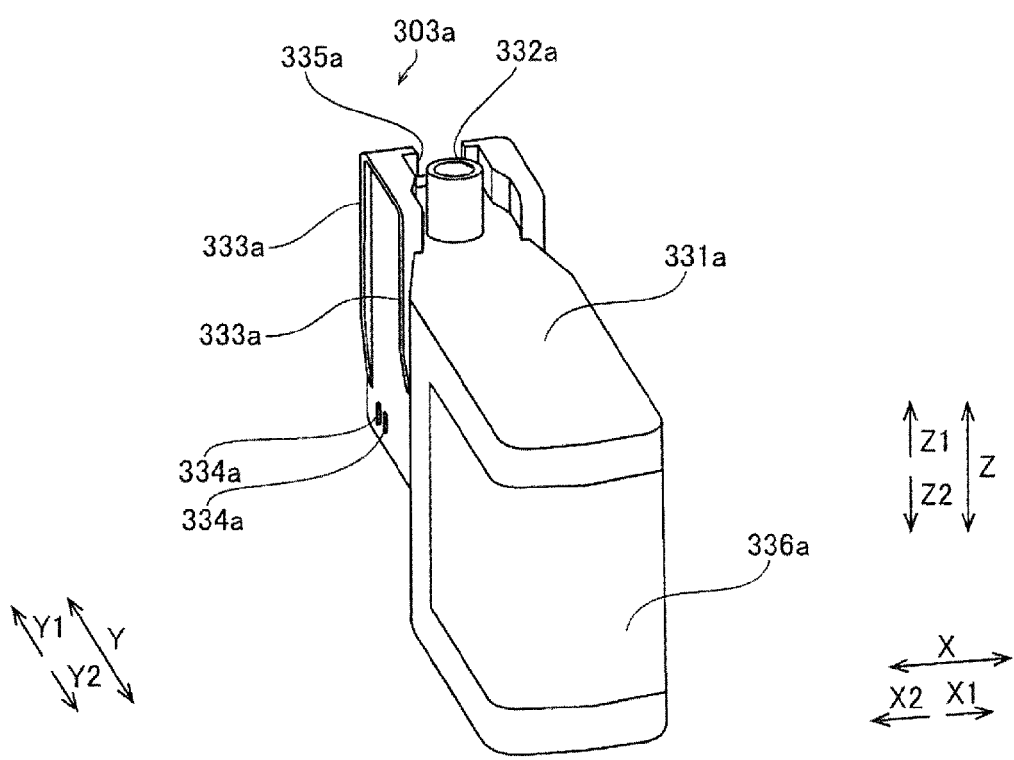
FIG. 21 is a perspective view of a first reagent container of a sample analysis system according to a second embodiment of the present invention.

As shown in FIG. 21, the first reagent container 303a includes a body portion 331a, an opening 332a, guided portions 333a, and claws 334a formed near the lower end of the first reagent container 303a. The first reagent container 303a includes a cutout 335a formed on the Y1 side and the Z1 side of the body portion 331a. To the first reagent container 303a, a label 336a indicating reagent information is attached so as to cover the side face on the Y2 side. A part of the label 336a is blue.

Figure 22:
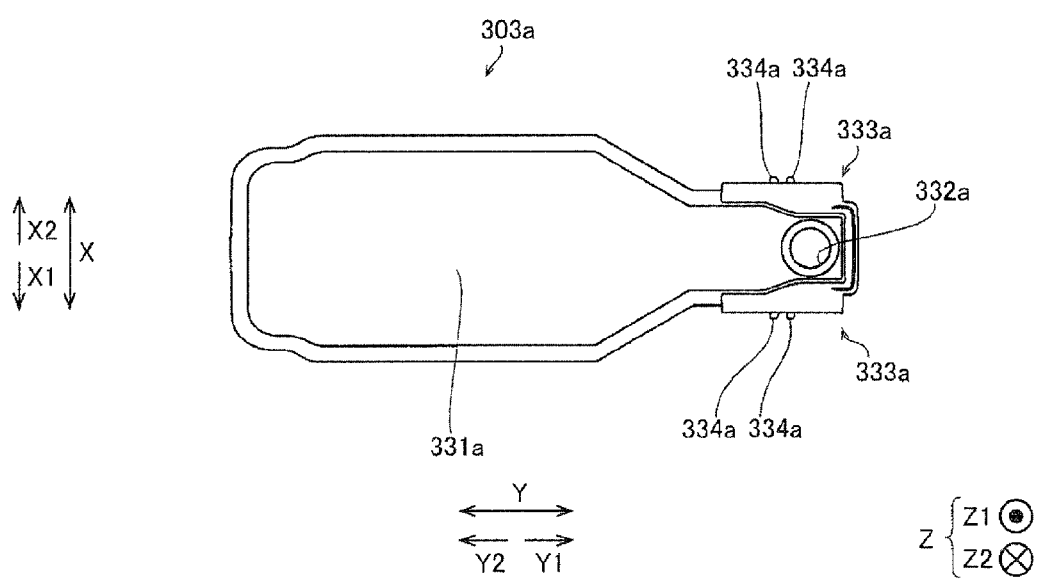
FIG. 22 is a plan view of the first reagent container of the sample analysis system according to the second embodiment of the present invention.

As shown in FIG. 22, the opening 332a is provided on the Z1 side of the body portion 331a. The opening 332a is provided near the end on the Y1 side of the body portion 331a.

Figure 23:
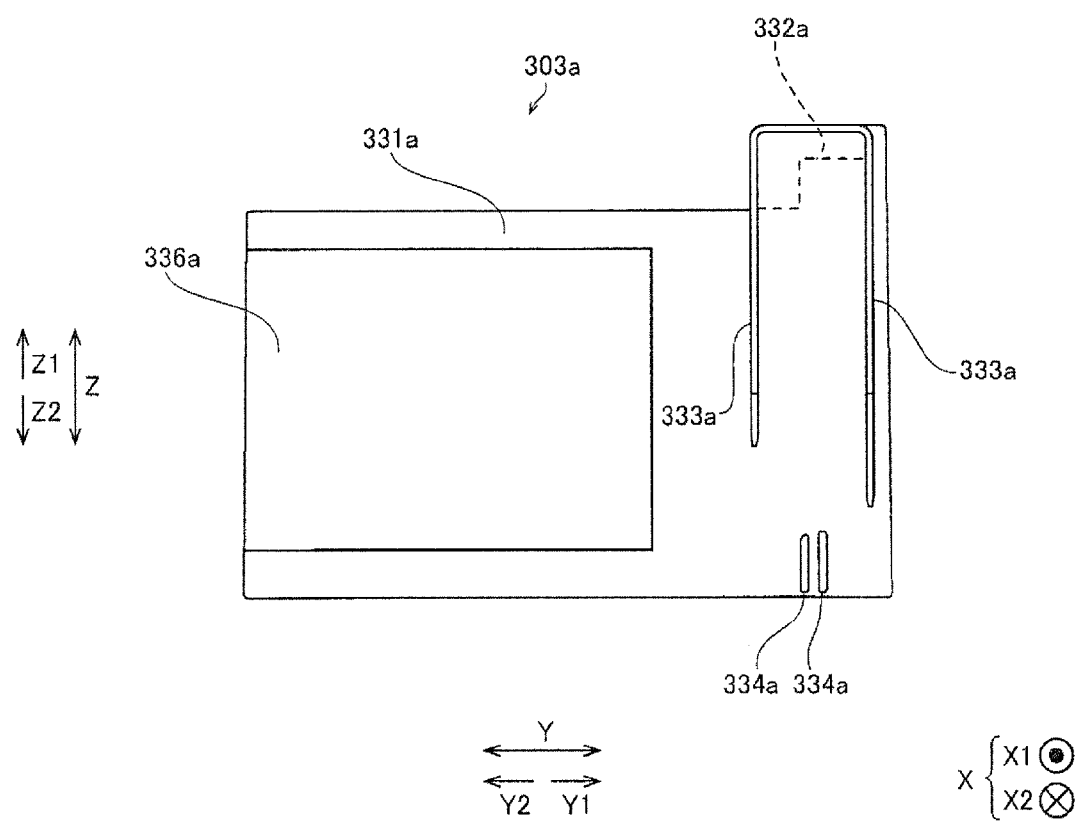
FIG. 23 is a side view of the first reagent container of the sample analysis system according to the second embodiment of the present invention.
Figure 24:
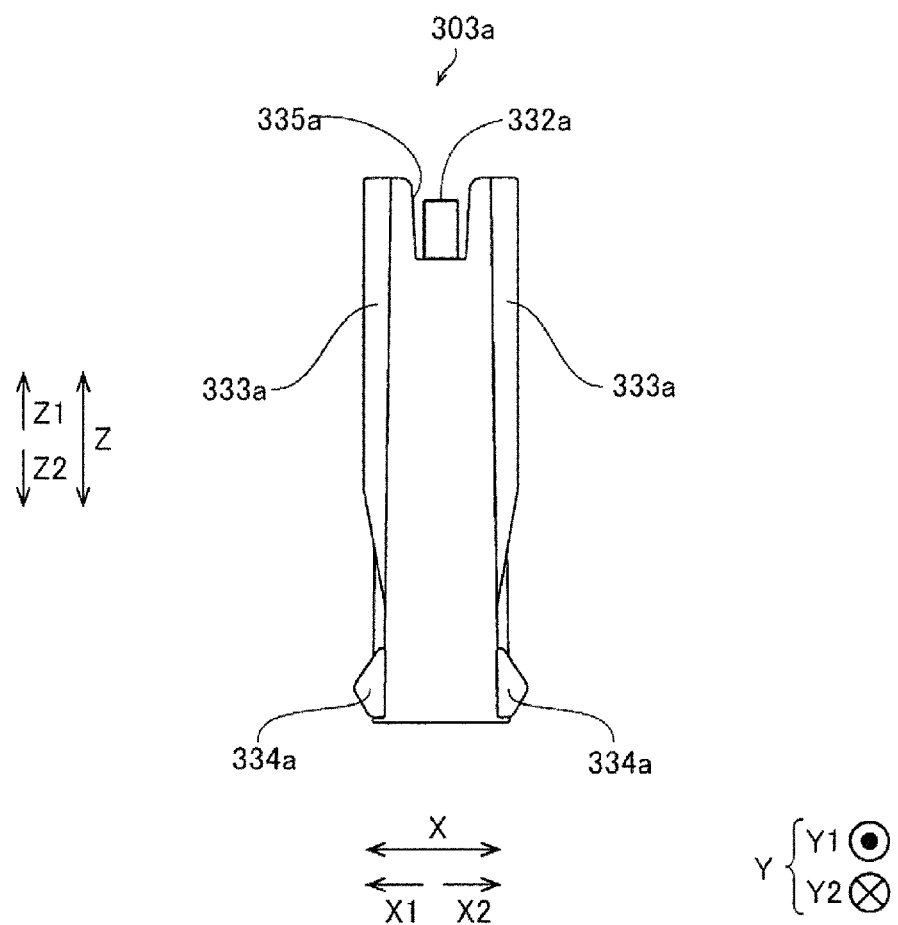
FIG. 24 is a view, seen from the Y1 side, of the first reagent container of the sample analysis system according to the second embodiment of the present invention.

The guided portions 333a are configured to guide the aspirating tube holder 224a relative to the first reagent container 303a such that the aspirating tube holder 224a is allowed to reach a state where the aspirating tube 223a has entered the first reagent container 303a or a state where the aspirating tube 223a has retreated from the first reagent container 303a. As shown in FIG. 23, the guided portions 333a are respectively provided on the outer faces on the X1 side and the X2 side of the body portion 331a.

Figure 25:
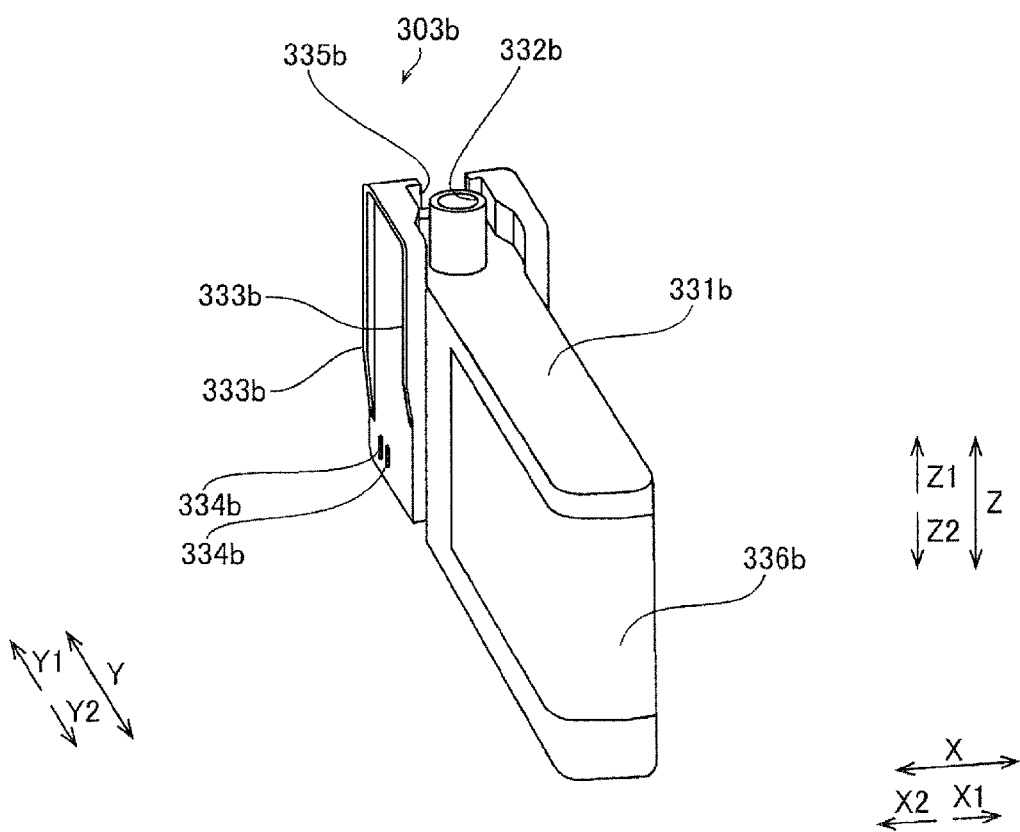
FIG. 25 is a perspective view of a second reagent container of the sample analysis system according to the second embodiment of the present invention.

As shown in FIG. 25, the second reagent container 303b includes a body portion 331b, an opening 332b, guided portions 333b, and claws 334b formed near the lower end of the second reagent container 303b. The second reagent container 303b includes a cutout 335b formed on the Z1 side of the body portion 331b. To the second reagent container 303b, a label 336b indicating reagent information is attached so as to cover the side face on the Y2 side. A part of the label 336b is red.

The opening 332b is provided on the Z1 side of the body portion 331b. The opening 332b is provided near the end on the Y1 side of the body portion 331b.

The guided portions 333b are configured to guide the aspirating tube holder 224b relative to the second reagent container 303b such that the aspirating tube holder 224b is allowed to reach a state where the aspirating tube 223b has entered the second reagent container 303b or a state where the aspirating tube 223b has retreated from the second reagent container 303b. The guided portions 333b are respectively provided on the outer faces on the X1 side and the X2 side of the body portion 331b.

The other configurations of the second embodiment are the same as those in the first embodiment.

It should be noted that the embodiments disclosed herein are merely illustrative in all aspects and should not be considered as being restrictive. The scope of the present disclosure is defined not by the description of the above embodiments but by the claims, and includes meaning equivalent to the claims and all modifications within the scope.

For example, in the first and second embodiments above, an example has been shown in which the present disclosure is applied to a sample analyzer which performs a test on a sample such as blood. However, the present disclosure is not limited thereto. The present disclosure can be applied to a sample analyzer which performs tests on a sample such as urine and genes.

In the first and second embodiments above, an example has been shown in which the aspirating tube holder includes an opening on the Y2 side. However, the present disclosure is not limited thereto. In the present disclosure, the aspirating tube holder may not include an opening on the Y2 side.

In the first and second embodiments above, an example has been shown in which two kinds of reagent containers; i.e., the first reagent container and the second reagent container, are set in the sample analysis system. However, the present disclosure is not limited thereto. In the present disclosure, one kind, or three or more kinds of reagent containers may be set in the sample analysis system.

In the first and second embodiments above, an example has been shown in which the color of the aspirating tube holder and the color of a part of the reagent container are the same. However, the present disclosure is not limited, thereto. In the present disclosure, the color of the aspirating tube holder and the color of a part of the reagent container may be similar to each other. Similar colors here means that two colors are visually recognized as of the same color type as in: blue-type colors such as blue, light blue, and purple, red-type colors such as red, orange, and pink, and the like.

What is claimed is:
1. A sample analyzer comprising:
   a reagent-container retainer having a bottom face surrounded by walls on both sides, at a front and at a rear thus forming a first surrounded space with a first opening on an upper face thereof, and the first surrounded space of the reagent-container retainer is configured to hold or retain a reagent container which has a second opening, wherein the reagent container is inserted into the first surrounded space through the first opening which is the upper face of the reagent-container retainer;
   a reagent container setting part configured to enable mounting of the reagent-container retainer in order to retain the reagent container in place, wherein the reagent-container retainer is a removable part separate from the reagent container setting part, and the reagent container setting part defines a second surrounded space having a bottom face for the mounting of the reagent-container retainer and the second surrounded space is surrounded by walls on both sides, at a front and at a rear;
   an aspirating tube configured to aspirate a reagent through the second opening of the reagent container;
   an aspirating tube holder configured to hold the aspirating tube;

a detection unit configured to measure a measurement sample containing a sample and the reagent and to prepare measurement data of the measurement sample, and a control unit configured to generate an analysis result by analyzing the measurement data, wherein:

the reagent-container retainer includes a guide configured to guide the aspirating tube holder such that the aspirating tube held by the holder is inserted into the second opening of the reagent-container retained by the reagent-container retainer, the rear wall of the second surrounded space which is proximal to the rear of the reagent container setting part includes a lower wall portion, such that the lower wall portion facilitates removal of the reagent-container retainer from the rear of reagent container setting part, the lower wall portion of the rear wall has a height equal to or smaller than a half of a height at an upper end of the reagent container when the reagent container retained by the reagent-container retainer is set in place in the reagent container setting part, and a height at an upper end of each of the two side walls and the front wall is greater than the height of the lower wall portion.

2. The sample analyzer of claim 1, wherein
the guide of the reagent-container retainer guides the aspirating tube holder to linearly move in a sliding manner.

3. The sample analyzer of claim 2, wherein
the guide comprises a rail.

4. The sample analyzer of claim 1, wherein
the aspirating tube holder is formed in a rectangular parallelepiped shape.

5. The sample analyzer of claim 4, wherein
the aspirating tube holder has an upper face surrounded by walls on both sides and at a front, with a third opening is provided in a rear face and a bottom face, the aspirating tube holder is mounted to the retainer by inserting the guide of the retainer into the third opening.

6. The sample analyzer of claim 1, further comprising:
a housing forming an outer shape of a body of the sample analyzer; and
a drawer part configured to allow the reagent container setting part to be put into and out of the housing.

7. The sample analyzer of claim 1, wherein
the reagent container setting part is configured to be able to have set therein the reagent container and a second reagent container different from the reagent container; and
the sample analyzer further comprises:
a second retainer configured to retain the second reagent container;
a second aspirating tube configured to aspirate a reagent in the second reagent container, and
a second aspirating tube holder configured to hold the second aspirating tube.

8. The sample analyzer of claim 7, wherein
a color of the aspirating tube holder is identical to a color of at least a part of the reagent container which the aspirating tube held by the aspirating tube holder enters.

9. The sample analyzer of claim 1, further comprising:
a reaction chamber, wherein
the aspirating tube is connected to the reaction chamber via a tube, and
the tube has a length that allows the aspirating tube holder to be taken out of the sample analyzer.

10. The sample analyzer of claim 1, wherein
the reagent container contains a staining liquid.

11. The sample analyzer of claim 3, wherein
the rail of the retainer is arranged in up-down directions, and
an upper end of the rail is provided above the second opening of the reagent container.

12. The sample analyzer of claim 1, wherein
the reagent-container retainer is configured to mount the aspirating tube holder to insert the aspirating tube into the second opening of the reagent container which is retained by the reagent-container retainer.

13. The sample analyzer of claim 12, wherein the detection unit measure the measurement sample by a flow cytometry.

14. The sample analyzer of claim 12, further comprising:
a reaction chamber, wherein
the aspirating tube is connected to the reaction chamber via a tube, and
the tube has a length that allows the aspirating tube holder to be taken out of the sample analyzer.

15. The sample analyzer of claim 12, wherein the reagent container contains a staining liquid.

16. The sample analyzer of claim 1, wherein the reagent-container retainer the aspirating tube holder having a second engage portion which is engaged with the first engage portion of the case when the aspirating tube holder is mounted on the reagent container retainer which retains the reagent container.

17. The sample analyzer of claim 16, wherein
the detection unit measure the measurement sample by a flow cytometry.

18. The sample analyzer of claim 16, wherein
the first engage portion comprises a claw and the second engage portion comprises a hole to be fitted with the claw.

19. The sample analyzer of claim 16, further comprising:
a reaction chamber, wherein
the aspirating tube is connected to the reaction chamber via a tube, and
the tube has a length that allows the aspirating tube holder to be taken out of the sample analyzer.

* * * * *

UNITED STATES PATENT AND TRADEMARK OFFICE
CERTIFICATE OF CORRECTION

PATENT NO. : 9,795,967 B2
APPLICATION NO. : 14/664182
DATED : October 24, 2017
INVENTOR(S) : Takaaki Nagai et al.

Page 1 of 1

It is certified that error appears in the above-identified patent and that said Letters Patent is hereby corrected as shown below:

In the Claims

In Column 14, Claim 16, Line 36, before "the aspirating tube holder" insert --having a first engage portion,--.

Signed and Sealed this
Fourteenth Day of August, 2018

Andrei Iancu
*Director of the United States Patent and Trademark Office*